United States Patent
Araki et al.

(10) Patent No.: US 12,331,013 B2
(45) Date of Patent: Jun. 17, 2025

(54) PRODUCTION METHOD FOR INDAN AND HYDRINDANE

(71) Applicant: ENEOS CORPORATION, Tokyo (JP)

(72) Inventors: Yasuhiro Araki, Tokyo (JP); Atsushi Segawa, Tokyo (JP); Yasuyuki Iwasa, Tokyo (JP); Tai Ohuchi, Tokyo (JP); Kazuya Mayumi, Tokyo (JP); Yukihiro Yoshiwara, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 83 days.

(21) Appl. No.: 18/270,921

(22) PCT Filed: Jan. 13, 2022

(86) PCT No.: PCT/JP2022/000952
§ 371 (c)(1),
(2) Date: Jul. 5, 2023

(87) PCT Pub. No.: WO2022/154048
PCT Pub. Date: Jul. 21, 2022

(65) Prior Publication Data
US 2024/0051899 A1    Feb. 15, 2024

(30) Foreign Application Priority Data
Jan. 15, 2021    (JP) ................................. 2021-004948

(51) Int. Cl.
| | | |
|---|---|---|
| *C07C 5/03* | (2006.01) | |
| *B01J 23/42* | (2006.01) | |
| *C07C 5/48* | (2006.01) | |
| *C07C 13/465* | (2006.01) | |

(52) U.S. Cl.
CPC ................. *C07C 5/03* (2013.01); *B01J 23/42* (2013.01); *C07C 5/48* (2013.01); *C07C 13/465* (2013.01); *C07C 2602/08* (2017.05)

(58) Field of Classification Search
CPC .......... B01J 23/42; C07C 13/465; C07C 5/03; C07C 5/48
See application file for complete search history.

(56) References Cited

FOREIGN PATENT DOCUMENTS

| | | | |
|---|---|---|---|
| JP | 2001-220359 A | 8/2001 | |
| JP | 2003-327551 A | 11/2003 | |
| JP | 2011-051951 A | 3/2011 | |
| JP | 2013-133293 A | 7/2013 | |
| WO | WO-2011027755 A1 * | 3/2011 | ........... C07C 13/465 |
| WO | 2019/176247 A1 | 9/2019 | |

OTHER PUBLICATIONS

Yanagawa reference (Year: 2011).*
ISR issued in International Patent Application No. PCT/JP2022/000952, Mar. 22, 2022, translation.
IPRP issued in International Patent Application No. PCT/JP2022/000952, Jul. 27, 2023, translation.

* cited by examiner

*Primary Examiner* — Sharon Pregler
(74) *Attorney, Agent, or Firm* — GREENBLUM & BERNSTEIN, P.L.C.

(57) ABSTRACT

Provided is a production method for indan and hydrindane, including a reaction step of introducing a raw material composition including tetrahydroindene into a continuous reactor including a solid catalyst containing platinum, and bringing the raw material composition into contact with the solid catalyst under the conditions of 150° C. to 350° C. to obtain a reaction product including indan and hydrindane, in which the amount (mol/min) of hydrogen molecules is 5 times or less the amount (mol/min) of tetrahydroindene, and the amount (mol/min) of oxygen molecules is 0.1 times or less the amount (mol/min) of tetrahydroindene.

9 Claims, No Drawings

PRODUCTION METHOD FOR INDAN AND HYDRINDANE

TECHNICAL FIELD

The present invention relates to a production method for indan and hydrindane.

BACKGROUND ART

Indan is known as a substance useful as a raw material for synthesizing pharmaceutical products, a raw material of metallocene catalysts, or the like. Regarding a production method for indan, for example, a method of producing indan by a dehydrogenation reaction of tetrahydroindene is known (for example, Patent Literature 1).

Furthermore, hydrindane has excellent solubility and is suitably used for use applications such as a solvent for paints, a cleaning agent, and the like. Regarding a production method for hydrindane, for example, a method of producing hydrindane by a hydrogenation reaction of tetrahydroindene is known (for example, Patent Literature 2).

CITATION LIST

Patent Literature

Patent Literature 1: Japanese Unexamined Patent Publication No. 2013-133293
Patent Literature 2: Japanese Unexamined Patent Publication No. 2011-051951

SUMMARY OF INVENTION

Technical Problem

It is an object of the present invention to provide a production method for indan and hydrindane, by which indan and hydrindane can be produced simultaneously and efficiently.

Solution to Problem

The inventors of the present invention found that both indan and hydrindane can be efficiently produced from a raw material composition including 3a,4,7,7a-tetrahydroindene in the presence of a specific catalyst and under specific reaction conditions, thus completing the present invention.

An aspect of the present invention relates to a production method for indan and hydrindane, including a reaction step of introducing a raw material composition including 3a,4,7,7a-tetrahydroindene into a continuous reactor including a solid catalyst containing platinum, and bringing the raw material composition into contact with the solid catalyst under conditions of 150° C. to 350° C. to obtain a reaction product including indan and hydrindane.

With regard to the production method, the amount (mol/min) of hydrogen molecules to be introduced into the continuous reactor per unit time is 5 times or less the amount (mol/min) of 3a,4,7,7a-tetrahydroindene to be introduced into the continuous reactor per unit time. Furthermore, with regard to the production method, the amount (mol/min) of oxygen molecules to be introduced into the continuous reactor per unit time is 0.1 times or less the amount (mol/min) of 3a,4,7,7a-tetrahydroindene to be introduced into the continuous reactor per unit time.

According to an embodiment, the reaction step may be a step of bringing the raw material composition into contact with the solid catalyst under conditions of 0.1 to 5.0 MPaG.

According to an embodiment, the solid catalyst may contain a carrier and a supported metal supported on the carrier, and the carrier may include aluminum, while the supported metal includes platinum.

According to an embodiment, a proportion occupied by the platinum in the supported metal may be 80% by mass or more.

According to an embodiment, the platinum may be supported on the carrier by using a platinum source that includes no chlorine atom.

According to an embodiment, a content of 3a,4,7,7a-tetrahydroindene in the raw material composition may be 5% by mass or more.

According to an embodiment, a mass ratio ($C_1/C_2$) of a content of indan $C_1$ with respect to a content of hydrindane $C_2$ in the reaction product may be 1.0 or more and 4.5 or less.

According to an embodiment, the reaction product may further include 3a,4,7,7a-tetrahydroindene, and a portion of the reaction product may be reused as the raw material composition of the reaction step.

The production method according to an embodiment may further include a raw material synthesis step of reacting butadiene with at least one selected from the group consisting of cyclopentadiene and dicyclopentadiene to obtain 3a,4,7,7a-tetrahydroindene.

Advantageous Effects of Invention

According to the present invention, there is provided a production method for indan and hydrindane, by which indan and hydrindane can be produced simultaneously and efficiently.

DESCRIPTION OF EMBODIMENTS

Suitable embodiments of the present invention will be described in detail below.

The production method for indan and hydrindane according to the present embodiment includes a reaction step of introducing a raw material composition including 3a,4,7,7a-tetrahydroindene (hereinafter, also referred to as "THI") into a continuous reactor including a solid catalyst containing platinum, and bringing the raw material composition into contact with the solid catalyst under the conditions of 150° C. to 350° C. to obtain a reaction product including indan and hydrindane.

In the production method of the present embodiment, the amount (mol/min) of hydrogen molecules to be introduced into the continuous reactor per unit time is 5 times or less the amount (mol/min) of THI to be introduced into the continuous reactor per unit time. Furthermore, in the production method of the present embodiment, the amount (mol/min) of hydrogen molecules to be introduced into the continuous reactor per unit time is 0.1 times or less the amount (mol/min) of THI to be introduced into the continuous reactor per unit time.

According to the production method of the present embodiment, indan and hydrindane can be produced simultaneously and efficiently.

In the production method of the present embodiment, by employing a specific solid catalyst and specific reaction conditions, the reaction of THI in the continuous reactor proceeds efficiently, and both indan and hydrindane can be obtained in a well-balanced manner.

Hereinafter, the solid catalyst according to the present embodiment will be described in detail.

The solid catalyst may be, for example, a catalyst containing a carrier and a supported metal supported on the carrier. At this time, it is preferable that the solid catalyst contains platinum as the supported metal.

The carrier is preferably a carrier including aluminum, and more preferably an inorganic oxide carrier including aluminum. The carrier may include alumina ($Al_2O_3$), may include alumina and an oxide of another element, or may include a composite oxide of aluminum and another element. Examples of the other element include silicon (Si), magnesium (Mg), tin (Sn), lead (Pb), zinc (Zn), selenium (Se), iron (Fe), and indium (In), and among these, preferably silicon (Si), magnesium (Mg), and tin (Sn) are preferred. As the alumina, γ-alumina is particularly preferred.

The specific surface area of the carrier may be, for example, 20 $m^2/g$ or more and is preferably 100 $m^2/g$ or more, and more preferably 150 $m^2/g$ or more. As a result, the catalytic activity tends to be further improved. Furthermore, the specific surface area of the carrier may be, for example, 500 $m^2/g$ or less and is preferably 400 $m^2/g$ or less, and more preferably 300 $m^2/g$ or less. As a result, the strength and shapeability of the carrier tend to be further improved. Incidentally, in the present specification, the specific surface area of the carrier is measured with a BET specific surface area meter using a nitrogen adsorption method.

With regard to the solid catalyst, the supported metal that is supported on the carrier may include platinum and may further include a metal other than platinum. Examples of the other metal include Pd, Re, Sn, Fe, Zn, Co, Ni, Ga, In, and Mn.

With regard to the solid catalyst, it is preferable that the supported metal is mainly platinum. Specifically, the proportion occupied by platinum in the supported metal may be, for example, 70% by mass or more and is preferably 80% by mass or more, and more preferably 90% by mass or more, and the proportion may be 95% by mass or more, 97% by mass or more, 99% by mass or more, or 99.5% by mass or more.

The content of the supported metal in the solid catalyst may be, from the viewpoint that the catalytic activity is further improved, for example, 0.1% by mass or more, and the content is preferably 0.2% by mass or more and may be 0.5% by mass or more, 1% by mass or more, or 1.5% by mass or more. Furthermore, from the viewpoint of having more excellent economic efficiency, the content of the supported metal in the solid catalyst may be, for example, 10% by mass or less, and is preferably 8% by mass or less, more preferably 6% by mass or less, even more preferably 4% by mass or less, and the content may also be 2% by mass or less or 1% by mass or less.

A suitable range of the content of platinum in the solid catalyst may be the same as a suitable range of the content of the supported metal.

The solid catalyst may be such that the supported metal is supported on the carrier by using a metal source. The metal source is preferably a metal source that includes no chlorine atom. As a result, corrosion of the apparatus is suppressed, and production of indan and hydrindane can be carried out more efficiently.

Examples of the metal source for supporting platinum (platinum source) include tetraammineplatinum(II) nitrate ($[Pt(NH_3)_4](NO_3)_2$), dinitrodiammineplatinum(II) ($Pt(NO_2)_2(NH_3)_2$), tetraammineplatinum(II) hydroxide ($[Pt(NH_3)_4](OH)_2$), hexaammineplatinum(IV) hydroxide ($[Pt(NH_3)_6](OH)_4$), hexaammineplatinum(IV) nitrate ($[Pt(NH_3)_6](NO_3)_4$), and tetraammineplatinum(II) acetate ($[Pt(NH_3)_4](CH_3COO)_2$). Among these, tetraammineplatinum(II) nitrate ($[Pt(NH_3)_4](NO_3)_2$), dinitrodiammineplatinum(II) ($Pt(NO_2)_2(NH_3)_2$), and tetraammineplatinum(II) hydroxide ($[Pt(NH_3)_4](OH)_2$) are particularly suitable as the platinum source.

A supporting method for the supported metal is not particularly limited, and for example, known supporting methods such as an impregnation method, a deposition method, a coprecipitation method, a kneading method, an ion exchange method, and a pore filling method can be used.

The shape of the solid catalyst is not particularly limited and can be appropriately selected according to the shape of the reactor or the like. The shape of the solid catalyst may be, for example, a pellet shape, a granular shape, a honeycomb shape, or a sponge shape.

Regarding the solid catalyst, one that has been subjected to a reduction treatment as a pretreatment may be used. The reduction treatment can be carried out by, for example, retaining the solid catalyst at 100° C. to 700° C. in the presence of a reducing gas. The retention time may be, for example, 10 minutes to 20 hours. Examples of the reducing gas include hydrogen and carbon monoxide. By using a solid catalyst that has been subjected to a reduction treatment, the induction period of the early stage of reaction can be shortened. Incidentally, the induction period refers to a state in which among the supported metals in the solid catalyst, fewer metals are in an active state, and the catalytic activity is low.

Next, the reaction step according to the present embodiment will be described in detail.

In the production method of the present embodiment, in the reaction step, a raw material composition including THI is introduced into a continuous reactor including a solid catalyst containing platinum, and the raw material composition is brought into contact with the solid catalyst under the conditions of 150° C. to 350° C. As a result, a hydrogen transfer reaction between THI molecules occurs, and a reaction product including indan and hydrindane is obtained.

The raw material composition may further contain components other than THI. Examples of the other components include an alkane, an olefin, an aromatic compound, and a hydride of THI.

The content of THI in the raw material composition is, from the viewpoint of having more excellent reactivity and economic efficiency, for example, 1% by mass or more, preferably 3% by mass or more, and more preferably 5% by mass or more, and the content may be 10% by mass or more, 30% by mass or more, 50% by mass or more, 70% by mass or more, 90% by mass or more, or 95% by mass or more, and may be 100% by mass.

The continuous reactor may be a reactor capable of a continuous reaction. Examples of the continuous reactor include a tubular reactor and a continuous stirred tank reactor.

The reaction mode of the reaction step is not particularly limited and may be, for example, a fixed bed type, a moving bed type, or a fluidized bed type. Among these, from the viewpoint of the facility cost, a fixed bed type is preferred.

With regard to the reaction step, the temperature at the time of bringing the raw material composition into contact with the solid catalyst (reaction temperature) is 150° C. or higher, preferably 170° C. or higher, more preferably 190° C. or higher, and even more preferably 200° C. or higher. When the reaction temperature is low, there is a tendency that the reaction is not likely to proceed. Furthermore, the reaction temperature is 350° C. or lower, preferably 320° C.

or lower, more preferably 300° C. or lower, and even more preferably 290° C. or lower. When the reaction temperature is high, there is a tendency that catalyst deterioration is likely to proceed. The reaction temperature can also be referred to as the temperature inside the reactor.

With regard to the reaction step, from the viewpoint that reactivity is further improved, the pressure at the time of bringing the raw material composition into contact with the solid catalyst (reaction pressure) may be, for example, 0.01 MPaG or higher, and the pressure is preferably 0.05 MPaG or higher, and more preferably 0.1 MPaG or higher, and may also be 0.7 MPaG or higher or 0.9 MPaG or higher. Furthermore, from the viewpoint of having more excellent economic efficiency, the reaction pressure may be, for example, 9.0 MPaG or lower, and the reaction pressure is preferably 7.0 MPaG or lower, more preferably 5.0 MPaG or lower, and even more preferably 3.0 MPaG or lower.

It is preferable that the conditions inside the reactor are conditions in which THI is a liquid. That is, it is preferable that the reaction step is a step of bringing a liquid raw material composition into contact with the solid catalyst.

With regard to the reaction step, from the viewpoint of having more excellent economic efficiency, WHSV may be, for example, 0.1 $h^{-1}$ or higher and is preferably 0.5 $h^{-1}$ or higher, more preferably 1.0 $h^{-1}$ or higher, and even more preferably 3.0 $h^{-1}$ or higher. Furthermore, from the viewpoint that reactivity is further improved, the WHSV may be, for example, 30 $h^{-1}$ or lower and is preferably 20 $h^{-1}$ or lower, more preferably 10 $h^{-1}$ or lower, and even more preferably 5.0 $h^{-1}$ or lower.

Incidentally, the WHSV represents the weight ratio of the supply amount per unit time of the raw material composition with respect to the solid catalyst packed in the reactor.

With regard to the reaction step, hydrogen gas, oxygen gas, air, an inert gas, or the like may be introduced into the continuous reactor together with the raw material composition.

With regard to the reaction step, the amount (mol/min) of hydrogen molecules to be introduced into the continuous reactor per unit time is 5 times or less the amount (mol/min) of THI to be introduced into the continuous reactor per unit time. In other words, the ratio ($C_{H2}/C_0$) of the amount $C_{H2}$ (mol/min) of hydrogen molecules to be introduced into the continuous reactor per unit time with respect to the amount $C_0$ (mol/min) of THI to be introduced into the continuous reactor per unit time is 5 or less. In the production method of the present embodiment, since indan and hydrindane are produced by a hydrogen transfer reaction between THI molecules, introduction of hydrogen into the continuous reactor is not necessarily required. When the amount of hydrogen gas introduced is too large, the yield of indan may be noticeably decreased.

The ratio ($C_{H2}/C_0$) is preferably 3 or less, more preferably 1 or less, even more preferably 0.5 or less, and even more preferably 0.1 or less, and may also be 0.

With regard to the reaction step, the amount (mol/min) of oxygen molecules to be introduced into the continuous reactor per unit time is 0.1 times or less the amount (mol/min) of THI to be introduced into the continuous reactor per unit time. In other words, the ratio ($C_{O2}/C_0$) of the amount $C_{O2}$ (mol/min) of oxygen molecules to be introduced into the continuous reactor per unit time with respect to the amount $C_0$ (mol/min) of THI to be introduced into the continuous reactor per unit time is 0.1 or less. In the production method of the present embodiment, since indan and hydrindane are produced by a hydrogen transfer reaction between THI molecules, introduction of oxygen into the continuous reactor is not required. When oxygen is introduced, the total yield of indan and hydrindane is decreased.

The ratio ($C_{O2}/C_0$) is preferably 0.05 or less, and more preferably 0.01 or less, and may also be 0.

In the reaction step, a reaction product including indan and hydrindane produced by the reaction of THI is obtained. Furthermore, the produced hydrindane may include a cis-form and a trans-form.

With regard to the reaction step, the conversion ratio of THI may be, for example, 70% or higher and is preferably 80% or higher, more preferably 85% or higher, even more preferably 95% or higher, and the conversion ratio may be 97% or higher, 98% or higher, or 99% or higher and may also be 100%.

With regard to the reaction step, the total selectivity of indan and hydrindane may be, for example, 10 mol % or more and is preferably 30 mol % or more, more preferably 50 mol % or more, and even more preferably 90 mol % or more, and the total selection ratio may also be 100 mol %. Incidentally, the total selection ratio of indan and hydrindane can be determined from the ratio of the total yield of indan and hydrindane with respect to the conversion ratio of THI.

The mass ratio ($C_1/C_2$) of the content $C_1$ of indan with respect to the content $C_2$ of hydrindane in the reaction product may be, for example, 0.5 or higher and is preferably 0.7 or higher, more preferably 1.0 or higher, and even more preferably 1.3 or higher, and the mass ratio may also be 1.5 or higher or 2.0 or higher. Furthermore, the mass ratio ($C_1/C_2$) may be, for example, 5 or lower and is preferably 4.7 or lower, more preferably 4.5 or lower, even more preferably 4.3 or lower, and still more preferably 4 or lower.

A portion of the reaction product may be reused as a portion of the raw material composition of the reaction step. As a result, the raw material composition is diluted, heat generation caused by a hydrogen transfer reaction is suppressed, catalyst deterioration caused by rapid heat generation is suppressed, and the production efficiency for indan and hydrindane in the entire process may be improved.

The production method of the present embodiment may further include a raw material synthesis step of reacting butadiene with at least one selected from the group consisting of cyclopentadiene and dicyclopentadiene to obtain THI.

Thus, suitable embodiments of the present invention have been described; however, the present invention is not intended to be limited to the above-described embodiments.

EXAMPLES

The present invention will be described in more detail by way of Examples; however, the present invention is not intended to be limited to these Examples.

Example 1

A commercially available γ-alumina (manufactured by SUMITOMO CHEMICAL COMPANY, LIMITED) was mixed with an aqueous solution of sodium stannate (manufactured by KISHIDA CHEMICAL Co., Ltd., $Na_2SnO_3 \cdot 3H_2O$). The obtained mixture was dried at 130° C. for 12 hours, subsequently calcined at 550° C. for 3 hours, and washed with ion-exchanged water. This washing operation was repeated three times, and a carrier was prepared. The tin oxide ($SnO_2$) content of the obtained carrier was 30% by mass. Platinum was impregnated and supported on this carrier by using a dinitrodiammineplatinum(II) nitric acid solution (manufactured by Tanaka Kikinzoku Kogyo, [$Pt(NH_3)_2(NO_2)_2$]/$HNO_3$) such that the platinum content was 3.0% by mass, and the obtained platinum-supported material was dried overnight at 130° C. and then calcined at 550° C. for 3 hours. Potassium was further impregnated and supported on the obtained calcination product by using an aqueous solution of potassium carbonate (manufactured by FUJIFILM Wako Pure Chemical Corporation, $K_2CO_3$) such that the content of potassium was 0.3% by mass, and the obtained potassium supported material was dried overnight at 130° C. and then calcined at 550° C. for 3 hours to obtain catalyst CAT-1.

1.0 g of the catalyst CAT-1 was packed in a tubular reactor, and the reaction tube was connected to a fixed bed flow type reaction apparatus. The reaction tube was heated to 300° C. at normal pressure, subsequently hydrogen was caused to flow at a rate of 50 mL/min for 60 minutes while maintaining the temperature, and a pretreatment of the catalyst was performed. Next, a raw material composition including THI was introduced into the reaction tube together with nitrogen gas or hydrogen gas as necessary, and the reaction was carried out under the conditions of the temperature, pressure, and WHSV described in Table 2.

The reaction product was sampled at a time point at which a predetermined time had passed from the initiation of the reaction (at the time of introducing the raw material composition), and the sample was analyzed by using a gas chromatograph (manufactured by SHIMADZU CORPORATION, GC-2014, FID-GC, column HP-1) equipped with a hydrogen flame detector. Based on the analysis results obtained using the gas chromatograph, each component (unit: % by mass) of the collected reaction product was quantitatively determined. The conversion ratio of THI after the lapse of a predetermined time, and the yields of indan and hydrindane were calculated from the numbers of moles of THI, indan, and hydrindane. Incidentally, the conversion ratio of THI is defined by the following Formula (1), the yield of indan is defined by Formula (2), and the yield of hydrindane is defined by Formula (3).

$$TC=\{1-(t1/t0)\}\times 100 \quad (1)$$

$$I=\{(i1-i0)/t0\}\times 100 \quad (2)$$

$$H=\{(h1-h0)/t0\}\times 100 \quad (3)$$

In the formulas, TC represents the conversion ratio (%) of THI; I represents the yield (%) of indan; H represents the yield (%) of hydrindane; t0 represents the number of moles of THI in the raw material composition; t1 represents the number of moles of THI in the reaction product; i1 represents the number of moles of indan in the reaction product; i0 represents the number of moles of indan in the raw material composition; h1 represents the number of moles of hydrindane in the reaction product; and h0 represents the number of moles of hydrindane in the raw material composition.

The composition of the catalyst is shown in Table 1. The reaction conditions and the measurement results are shown in Table 2.

Example 2

Production of indan and hydrindane was carried out in the same manner as in Example 1, except that the same catalyst as that of Example 1 was used, and the reaction conditions were changed as described in Table 2. The results are shown in Table 2.

Example 3

Production of indan and hydrindane was carried out in the same manner as in Example 1, except that the same catalyst as that of Example 1 was used, and the reaction conditions were changed as described in Table 2. The results are shown in Table 2.

Example 4

Platinum was impregnated and supported on zeolite H-MFI ($SiO_2/Al_2O_3$=1500) manufactured by Tosoh Corporation by using a dinitrodiammineplatinum(II) nitric acid solution (manufactured by Tanaka Kikinzoku Kogyo, [Pt$(NH_3)_2(NO_2)_2$]/$HNO_3$) such that the platinum content was 1.0% by mass, and the obtained platinum-supported material was dried overnight at 130° C. and then calcined at 550° C. for 3 hours to obtain CAT-2.

Production of indan and hydrindane was carried out in the same manner as in Example 1, except that CAT-2 was used as the catalyst, and the reaction conditions were set to the conditions described in Table 3. The results are shown in Table 3.

Example 5

20.0 g of a commercially available γ-alumina (NEOBEADS manufactured by Mizusawa Industrial Chemicals, Ltd.) was mixed with an aqueous solution obtained by dissolving 25.1 g of magnesium nitrate hexahydrate (manufactured by Wako Pure Chemical Industries, Ltd., Mg$(NO_3)_2 \cdot 6H_2O$) in 150 ml of water. The obtained mixed liquid was stirred at 50° C. for 180 minutes, and then water was removed under reduced pressure by using an evaporator. Thereafter, the obtained mixture was dried overnight at 130° C. and then calcined at 550° C. for 3 hours and subsequently calcined at 800° C. for 3 hours. The obtained calcination product was mixed with an aqueous solution obtained by dissolving 25.1 g of magnesium nitrate hexahydrate (manufactured by Wako Pure Chemical Industries, Ltd., Mg$(NO_3)_2 \cdot 6H_2O$) in 150 ml of water, the mixture was stirred at 50° C. for 180 minutes, and then water was removed under reduced pressure by using an evaporator.

Subsequently, the obtained mixture was dried overnight at 130° C. and then calcined at 550° C. for 3 hours and subsequently calcined at 800° C. for 3 hours. As a result, an alumina-magnesia carrier having a spinel type structure was obtained. Incidentally, for the obtained alumina-magnesia carrier, diffraction peaks originating from Mg spinel were confirmed at 2θ=36.9, 44.8, 59.4, and 65.3 deg by X-ray diffraction measurement (X-ray source: CuKα, apparatus: manufactured by Rigaku Corporation, RINT 2500). Platinum was impregnated and supported on this Mg spinel carrier by using a dinitrodiammineplatinum(II) nitric acid solution (manufactured by Tanaka Kikinzoku Kogyo, [Pt$(NH_3)_2(NO_2)_2$]/$HNO_3$) such that the platinum content was 0.5% by mass, and the obtained platinum-supported material was dried overnight at 130° C. and then calcined at 550° C. for 3 hours to obtain CAT-3.

Production of indan and hydrindane was carried out in the same manner as in Example 1, except that CAT-3 was used as the catalyst, and the reaction conditions were changed as described in Table 3. The results are shown in Table 3.

Example 6

Production of indan and hydrindane was carried out in the same manner as in Example 1, except that 0.5% Pt/alumina spheres (CAT-4) manufactured by N.E. CHEMCAT COR- PORATION were used as the catalyst, and the reaction conditions were changed as described in Table 3. The results are shown in Table 3.

Example 7

Production of indan and hydrindane was carried out in the same manner as in Example 1, except that 0.5% Pt/alumina pellets (CAT-5) manufactured by N.E. CHEMCAT CORPORATION were used as the catalyst, and the reaction conditions were changed as described in Table 3. The results are shown in Table 3.

Example 8

Platinum was impregnated and supported on a commercially available γ-alumina (manufactured by SUMITOMO CHEMICAL COMPANY, LIMITED) by using a dinitrodiammineplatinum(II) nitric acid solution (manufactured by Tanaka Kikinzoku Kogyo, $[Pt(NH_3)_2(NO_2)_2]/HNO_3$) such that the platinum content was 0.5% by mass, and the obtained platinum-supported material was dried overnight at 130° C. and then calcined at 550° C. for 3 hours to obtain CAT-6.

Production of indan and hydrindane was carried out in the same manner as in Example 1, except that CAT-6 was used as the catalyst, and the reaction conditions were changed as described in Table 4. The results are shown in Table 4.

Example 9

Production of indan and hydrindane was carried out in the same manner as in Example 1, except that CAT-6, which was the same catalyst as that of Example 8, was used, and the reaction conditions were changed as described in Table 4. The results are shown in Table 4.

Example 10

Production of indan and hydrindane was carried out in the same manner as in Example 1, except that CAT-6, which was the same catalyst as that of Example 8, was used, and the reaction conditions were changed as described in Table 4. The results are shown in Table 4.

Example 11

Production of indan and hydrindane was carried out in the same manner as in Example 1, except that CAT-6, which was the same catalyst as that of Example 8, was used, and the reaction conditions were changed as described in Table 5. Incidentally, the raw material composition was a composition including 10% by mass of THI, 63% by mass of indan, and 21% by mass of hydrindane. The results are shown in Table 5.

Example 12

Production of indan and hydrindane was carried out in the same manner as in Example 1, except that CAT-6, which was the same catalyst as that of Example 8, was used, and the reaction conditions were changed as described in Table 5. Incidentally, the initial raw material composition was a composition including 10% by mass of THI, 61% by mass of indan, and 27% by mass of hydrindane. Furthermore, while the THI concentration of the raw material composition was maintained at 10% by mass, a reaction was carried out by recycling a portion of the obtained reaction product as the raw material composition. For this reason, the composition of the raw material composition changed along with the progress of the reaction, and the raw material composition at 1900 h became a composition including 10% by mass of THI, 53% by mass of indan, and 16% by mass of hydrindane. The results are shown in Table 5.

Comparative Example 1

Production of indan and hydrindane was carried out in the same manner as in Example 1, except that CAT-1, which was the same catalyst as that of Example 1, was used, and the reaction conditions were changed as described in Table 6. The results are shown in Table 6.

Comparative Example 2

Production of indan and hydrindane was carried out in the same manner as in Example 1, except that CAT-1, which was the same catalyst as that of Example 1, was used, and the reaction conditions were changed as described in Table 6. The results are shown in Table 6.

Comparative Example 3

Production of indan and hydrindane was carried out in the same manner as in Example 1, except that no catalyst was used, and the reaction conditions were changed as described in Table 6. The results are shown in Table 6.

Comparative Example 4

Production of indan and hydrindane was carried out in the same manner as in Example 1, except that zeolite H-MFI ($SiO_2/Al_2O_3$=1500) manufactured by Tosoh Corporation was used as catalyst CAT-7, and the reaction conditions were changed as described in Table 6. The results are shown in Table 6.

TABLE 1

| Catalyst | |
| --- | --- |
| CAT-1 | 3% Pt-0.3% K/70% $Al_2O_3$-30% $SnO_2$ |
| CAT-2 | 1% Pt/H-MFI |
| CAT-3 | 0.5% Pt/$MgAl_2O_4$ |
| CAT-4 | 0.5% Pt/alumina spheres |
| CAT-5 | 0.5% Pt/alumina pellets |
| CAT-6 | 0.5% Pt/$Al_2O_3$ |
| CAT-7 | H-MFI |

TABLE 2

| | | Example 1 | Example 2 | Example 3 |
| --- | --- | --- | --- | --- |
| Catalyst | | CAT-1 | CAT-1 | CAT-1 |
| Reaction temperature | ° C. | 180 | 250 | 250 |
| Reaction pressure | MPaG | 0.15 | 0.75 | 0.15 |
| Raw material THI concentration | % by mass | 99 | 99 | 99 |

TABLE 2-continued

| | | Example 1 | | | Example 2 | | Example 3 | | |
|---|---|---|---|---|---|---|---|---|---|
| WHSV | 1/h | 3 | | | 3 | | 3 | | |
| H$_2$/THI | Molar ratio | 0 | | | 0 | | 0 | | |
| O$_2$/THI | Molar ratio | 0 | | | 0 | | 0 | | |
| N$_2$/THI | Molar ratio | 0.3 | | | 0 | | 0 | | |
| Elapsed time | h | 2 | 4 | 6 | 4 | 26 | 2 | 4.5 | 24 |
| THI conversion ratio | % | 100 | 100 | 100 | 100 | 100 | 97 | 91 | 80 |
| Yield I | % | 46 | 45.5 | 45 | 63.5 | 58 | 63 | 53 | 34 |
| Yield H | % | 21 | 19.5 | 18 | 25 | 16.5 | 16 | 14 | 4 |
| Yield I/yield H | | 2.2 | 2.3 | 2.5 | 2.5 | 3.5 | 3.9 | 3.8 | 8.5 |

TABLE 3

| | | Example 4 | | | Example 5 | | | Example 6 | | | Example 7 | | |
|---|---|---|---|---|---|---|---|---|---|---|---|---|---|
| Catalyst | | CAT-2 | | | CAT-3 | | | CAT-4 | | | CAT-5 | | |
| Reaction temperature | °C. | 250 | | | 250 | | | 250 | | | 250 | | |
| Reaction pressure | MPaG | 0.5 | | | 0.5 | | | 0.5 | | | 0.5 | | |
| Raw material THI concentration | % by mass | 99 | | | 99 | | | 99 | | | 99 | | |
| WHSV | 1/h | 3 | | | 3 | | | 10 | | | 10 | | |
| H$_2$/THI | Molar ratio | 0 | | | 0 | | | 0 | | | 0 | | |
| O$_2$/THI | Molar ratio | 0 | | | 0 | | | 0 | | | 0 | | |
| N$_2$/THI | Molar ratio | 0 | | | 0 | | | 0 | | | 0 | | |
| Elapsed time | h | 5 | 28 | 5 | 27 | 49 | 4 | 22 | 46 | 4 | 22 | | |
| THI conversion ratio | % | 100 | 100 | 100 | 100 | 100 | 99 | 95 | 94 | 99 | 89 | | |
| Yield I | % | 60 | 62 | 72 | 66 | 66 | 66 | 54 | 48 | 67 | 46 | | |
| Yield H | % | 27 | 25.5 | 25 | 30 | 31 | 25 | 18 | 11 | 22 | 16 | | |
| Yield I/yield H | | 2.2 | 2.4 | 2.9 | 2.2 | 2.1 | 2.6 | 3.0 | 4.4 | 3.0 | 2.9 | | |

TABLE 4

| | | Example 8 | | | Example 9 | | | Example 10 | | |
|---|---|---|---|---|---|---|---|---|---|---|
| Catalyst | | CAT-6 | | | CAT-6 | | | CAT-6 | | |
| Reaction temperature | °C. | 250 | | | 250 | | | 250 | | |
| Reaction pressure | MPaG | 0.9 | | | 0.9 | | | 0.9 | | |
| Raw material THI concentration | % by mass | 99 | | | 99 | | | 99 | | |
| WHSV | 1/h | 10 | | | 10 | | | 3 | | |
| H$_2$/THI | Molar ratio | 0 | | | 1 | | | 0 | | |
| O$_2$/THI | Molar ratio | 0 | | | 0 | | | 0 | | |
| N$_2$/THI | Molar ratio | 1 | | | 0 | | | 0 | | |
| Elapsed time | h | 4 | 24 | 4 | 22 | 46 | 7 | 24 | 177 | |
| THI conversion ratio | % | 100 | 100 | 100 | 99.5 | 98 | 100 | 100 | 100 | |
| Yield I | % | 75 | 74 | 53 | 49 | 43 | 66.5 | 68 | 65 | |
| Yield H | % | 21 | 23 | 44 | 46 | 35.5 | 29.5 | 29 | 27.5 | |
| Yield I/yield H | | 3.6 | 3.2 | 1.2 | 1.1 | 1.2 | 2.3 | 2.3 | 2.4 | |

TABLE 5

| | | Example 11 | Example 12 |
|---|---|---|---|
| Catalyst | | CAT-6 | CAT-6 |
| Reaction temperature | °C. | 250 | 230 |
| Reaction pressure | MPaG | 0.5 | 2.5 |
| Raw material THI concentration | % by mass | 10 | 10 |
| WHSV | 1/h | 5 | 10 |
| H$_2$/THI | Molar ratio | 0 | 0 |
| O$_2$/THI | Molar ratio | 0 | 0 |
| N$_2$/THI | Molar ratio | 0 | 0 |

TABLE 5-continued

|  |  | Example 11 | | | | Example 12 | | | |
| --- | --- | --- | --- | --- | --- | --- | --- | --- | --- |
| Elapsed time | h | 6 | 28 | 51 | 74 | 5 | 93 | 693 | 1972 |
| THI conversion ratio | % | 100 | 100 | 100 | 100 | 100 | 100 | 100 | 100 |
| Yield I | % | 68 | 63 | 63 | 61 | 68 | 65 | 58 | 56 |
| Yield H | % | 41 | 46 | 47 | 51 | 31 | 28 | 15 | 12 |
| Yield I/yield H | | 2.5 | 2.4 | 2.4 | 2.3 | 2.2 | 2.3 | 2.6 | 3.4 |

TABLE 6

|  |  | Comparative Example 1 | Comparative Example 2 | Comparative Example 3 | Comparative Example 4 | |
| --- | --- | --- | --- | --- | --- | --- |
| Catalyst | | CAT-1 | CAT-1 | — | CAT-7 | |
| Reaction temperature | ° C. | 550 | 140 | 180 | 350 | |
| Reaction pressure | MPaG | 0.1 | 0.15 | 0.15 | 0.15 | |
| Raw material THI concentration | % by mass | 99 | 99 | 99 | 99 | |
| WHSV | 1/h | 3 | 3 | 3 | 3 | |
| $H_2$/THI | Molar ratio | 1.1 | 0 | 0 | 0 | |
| $O_2$/THI | Molar ratio | 0 | 0 | 0 | 0 | |
| $N_2$/THI | Molar ratio | 0 | 0.3 | 0.3 | 0.3 | |
| Elapsed time | h | 3 | 2 | 4 | 2 | 4 |
| THI conversion ratio | % | 50 | 39 | 0 | 46 | 20 |
| Yield I | % | 3 | 20 | 0 | 13.8 | 0.4 |
| Yield H | % | 1 | 6.7 | 0 | 1.8 | 0.8 |
| Yield I/yield H | | 3.0 | 3.0 | — | 7.7 | 0.5 |

The invention claimed is:

1. A production method for indan and hydrindane, comprising:
reacting by introducing a raw material composition including 3a,4,7,7a-tetrahydroindene, optionally hydrogen molecules, and optionally oxygen molecules into a continuous reactor including a solid catalyst containing platinum, and bringing the raw material composition into contact with the solid catalyst under conditions of 150° C. to 350° C. to obtain a reaction product including indan and hydrindane,
wherein a ratio ($C_{H2}/C_0$) of an amount $C_{H2}$(mol/min) of the hydrogen molecules introduced into the continuous reactor per unit time with respect to an amount $C_0$(mol/min) of the 3a,4,7,7a-tetrahydroindene introduced into the continuous reactor per unit time is 1 or less, and
a ratio ($C_{O2}/C_0$) of an amount $C_{O2}$(mol/min) of the oxygen molecules introduced into the continuous reactor per unit time with respect to an amount $C_0$ of the 3a,4,7,7a-tetrahydroindene introduced into the continuous reactor per unit time is 0.1 or less.

2. The production method according to claim 1, wherein in the reacting, the raw material composition is brought into contact with the solid catalyst under conditions of 0.1 to 5.0 MPaG.

3. The production method according to claim 1, wherein the solid catalyst contains a carrier and a supported metal supported on the carrier, and the carrier includes aluminum, while the supported metal includes platinum.

4. The production method according to claim 3, wherein a proportion occupied by platinum in the supported metal is 80% by mass or more.

5. The production method according to claim 3, wherein the platinum is supported on the carrier by using a platinum source that includes no chlorine atom.

6. The production method according to claim 1, wherein a content of 3a,4,7,7a-tetrahydroindene in the raw material composition is 5% by mass or more.

7. The production method according to claim 1, wherein a mass ratio ($C_1/C_2$) of a content $C_1$ of indan with respect to a content $C_2$ of hydrindane in the reaction product is 1.0 or more and 4.5 or less.

8. The production method according to claim 1, wherein the reaction product further includes 3a,4,7,7a-tetrahydroindene, and a portion of the reaction product is reused as the raw material composition of the reacting.

9. The production method according to claim 1, further comprising raw material synthesis by reacting butadiene with at least one selected from the group consisting of cyclopentadiene and dicyclopentadiene to obtain 3a,4,7,7a-tetrahydroindene.

* * * * *